(12) United States Patent
Wager et al.

(10) Patent No.: US 6,541,249 B2
(45) Date of Patent: Apr. 1, 2003

(54) IMMORTALIZED HUMAN STROMAL CELL LINES

(75) Inventors: Ruth E. Wager, Rockville, MD (US); Maria Ourmanova, Boyds, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 27 days.

(21) Appl. No.: 09/740,789

(22) Filed: Dec. 21, 2000

(65) Prior Publication Data

US 2002/0001826 A1 Jan. 3, 2002

Related U.S. Application Data

(60) Provisional application No. 60/174,611, filed on Jan. 5, 2000, and provisional application No. 60/171,508, filed on Dec. 22, 1999.

(51) Int. Cl.$^7$ .......................... A01N 63/00; C12N 5/00; C12N 5/06

(52) U.S. Cl. ................... 435/325; 435/366.2; 435/377; 435/404; 435/405

(58) Field of Search .............................. 435/405, 366.2, 435/325

*Primary Examiner*—Christina Chan
*Assistant Examiner*—Michail A Belyavskyi
(74) *Attorney, Agent, or Firm*—Human Genome Sciences, Inc.

(57) ABSTRACT

A method for the culture of hematopoietic cells and/or production of human cytokines using immortalized human stromal cell lines is provided. These immortalized stromal cell lines condition media such that the ability of the hematopoietic stem cells to self-replicate and/or differentiate is maintained by the media or the ability of the committed progenitors to expand and/or differentiate is maintained by the media. Further provided are irradiated and non-irradiated immortalized human stromal cells that synthesize cytokines, such as, IL-7, IL-8, IL-11, FLT3L, SCF, LIF, M-CSF, TGF-beta 1, GM-CSF, MIP-1alpha, G-CSF, and MCP-1.

9 Claims, No Drawings

IMMORTALIZED HUMAN STROMAL CELL LINES

This application claims benefit under 35 U.S.C. §119(e) of the filing dates of copending U.S. Provisional Application Ser. No. 60/171,508, filed on Dec. 22, 1999, and copending U.S. Provisional Application Ser. No. 60/174,611, filed on Jan. 5, 2000, each of which is hereby incorporated by reference in its entirety.

BACKGROUND OF THE INVENTION

Hematopoietic cells are believed to originate in the bone marrow from primitive, undifferentiated precursors called totipotent stem cells. Totipotent stem cells give rise to more mature precursor cells called pluripotent stem cells. Pluripotent stem cells are able to self-renew and, thus, give rise to identical types of pluripotent stem cells. Further, pluripotent cells differentiate into two major stem cell lineages; myeloid stem cells or lymphoid stem cells. Once stem cells are committed to a given lineage they can only give rise to cells of that same lineage (these cells are called committed or dedicated "progenitors"). Of the two main lineages, myeloid cells may mature into red blood cells, granulocytes, monocytes, or megakaryocytes whereas lymphoid cells may mature into either B lymphocytes (B-cells) or T lymphocytes (T-cells).

The bone marrow microenvironment provides signals which regulate early stage stem cell maturation. These signals induce the progenitor cells to divide and differentiate. Thus, defining the functional components of the bone marrow microenvironment is a prerequisite to understanding how the proliferation and differentiation of progenitor cells is coordinately regulated. The cellular complexity of the marrow microenvironment has been demonstrated both in situ and in vitro by a variety of histochemical techniques (Lichtman, Exp. Hematol. 9:391 (1981), and Allen et al., Exp. Hematol. 12: 517 (1984)). The marrow microenvironment is comprised of both hematopoietic and stromal or mesenchymal derived cells. The stromal cells include endothelial cells that form the sinuses and adventitial reticular cells that have characteristics consistent with adipocytes, fibroblasts, and muscle cells (Charbord et al., Blood 66: 1138 (1985), and Charbord et al., Exp. Hematol. 18: 276 (1990)). Numerous advances in recent years have provided considerable information on the ontogeny and development of hematopoietic cells; however, ontogeny of the stromal components and their precise role in controlling hematopoiesis has proven elusive (Ogawa, Blood 81: 2844 (1993); Muller-Sieburg et al., Critical Rev. Immunol. 13: 115 (1993); and Dorshkind, Ann. Rev. Immunol. 8:111 (1990)).

Mesenchymal or "stromal" cells constitute a critical part of the bone marrow microenvironment. Stromal cells act (at least in part) by secreting soluble growth factors and cytokines that stimulate stem cell proliferation and differentiation. Some cytokines known to affect proliferation, differentiation, and function of hematopoietic cells include: bFGF (Huang et al., Nature, 360, 745 (1992)); FLT3L (Hannum et al., Nature, 368, 643 (1994); Lyman, Int. J. Hematol., 62, 63 (1995)); G-CSF (Ikebuchi et al., PNAS USA, 85, 3445 (1988)); GM-CSF (Brandt et al., J. Clin. Invest., 86, 932 (1990)); IL-1alpha (March, et al., Nature, 315, 641 (1985); Clemens, et al., Lymphokines and Interferons, A Practical Approach, 1, 272 (1987); IL-1beta (March, et al., Nature, 315, 641 (1985); Auron, et al., Proc. Natl. Acad. Sci. USA, 81, 7907 (1984); Clemens, et al., Lymphokines and Interferons, A Practical Approach, 1, 272 (1987); IL-1 and IL-6 (Brandt et al., J. Clin. Invest., 82, 1017 (1988); IL-3 (Leary et. al., Blood, 71, 1759(1988)); IL-7 (Goodwin, et al., Proc. Natl. Acad. Sci. USA, 86, 302 (1989); Yokota, et al., Proc. Natl. Acad. Sci. USA, 83, 5894 (1986)). IL-8 (Matsushima, et al., J. Exp. Med., 167, 1883 (1988); Schroeder, et al., J. Immunol., 139, 3474 (1987). IL-11 (Paul et al., PNAS USA, 87, 7512 (1990); Tsuji et al., PNAS USA, 87, 7512 (1990); LIF (Fletcher et. al., Blood, 76, 1098 (1990)); MCP-1 (Yoshimura, et al., FEBS Lett., 244, 487 (1989); Matsushima, et al., J. Exp. Med., 169, 1485 (1989)); M-CSF (Wong, et al., Science, 235, 1504 (1987); Halenbeck, et al., Biotechnology, 7, 710 (1989)); MIP-1alpha (Wolpe, et al., FASEB J., 3, 2565 (1989); Graham, et al., 344, 442 (1990)); SCF (Brandt et al., Blood, 79, 634 (1992); Zsebo et al., Cell, 63, 195 (1990)); TGF-beta1 (Tsang, et al., Cytokine, 7, 389 (1995)); TNF-alpha (Clemens, et al., Nature, 312, 724 (1984); Matthews, et al., Lymphokines and Interferons, A Practical Approach, 1, 221 (1987)); Tpo (Foster, et al., Proc. Natl. Acad. Sci. USA, 91, 13023 (1994); Avanzi, et al., Br. J. Haematol., 69, 359 (1988); Lok, et al., Stem Cells, 12, 586 (1994)).

Following initial evolution in the bone marrow, hematopoietic cells move to the peripheral circulation and into a variety organs (such as the thymus, liver, and spleen) where they further mature to terminally differentiated immune cells.

In contrast to the in vivo situation, long-term propagation of proliferating and/or differentiating hematopoietic stem cells in vitro is problematic. Due to the heterogeneous nature of the bone marrow microenvironment, it is extremely difficult to distinguish the subset of factors necessary and sufficient to recapitulate in vivo bone marrow conditions.

Long term cultures of marrow cells in vitro can approximate some conditions of the in vivo marrow microenvironment and have been informative with respect to the identification of growth factors, adhesion proteins and extracellular matrix proteins that mediate the interaction between the hematopoietic cells and the stromal elements (Muller-Sieburg et al., supra; Dorshkind, supra; Liesveld et al., Exp. Hematol. 9: 391 (1981); Kittler et al., Blood 79: 3168 (1992); Eaves et al., Blood 78: 110 (1991); Clark et al., Bailliere's Clin. Haematol. 5: 619 (1992); and Heinrich et al., Blood 82: 771 (1993)). One improvement to this system incorporated the use of stromal precursors, positive for the STRO-1 antigen, to initiate long term cultures (LTC); STRO-1 positive stromal precursors are devoid of myeloid components and less heterogeneous than primary cultures, but are still capable of supporting hematopoiesis (Simmons and Torok-Storb, Blood 78: 55–62 (1991)). However, both the STRO-1 initiated cultures and the primary LTC are too complex to delineate contributions from individual cell types. Moreover, primary cultures can be highly variable and change with time, further complicating the identification of stromal cells that have a role in controlling hematopoiesis.

Immortalized stromal cell lines have been used to circumvent some of these problems (Zipori et al., J. Cell Physiol. 118: 143 (1984); Zipori et al., J. Cell Physiol. 122: 81 (1985); Song et al., Exp. Hematol. 12:523 (1984)). In contrast to mouse cell lines, however, human cell lines undergo senescence unless first immortalized by transformation (for example, by introducing a retrovirus; see Lanotte et al., J. Cell Sci. 50: 281 (1981)). The first few human bone marrow stromal cell lines available were established using the SV40 virus large T antigen (Harigaya et al., Proc. Natl. Acad. Sci. USA 82: 3477 (1985); Tsai et al., J. Cell Physiol. 127: 137 (1986); Novotny et al., Exp. Hematol. 18: 775 (1990); Slack et al., Blood 75: 2319 (1990); Singer et al., Blood 70: 464 (1987); Cicutinni et al., Blood 80: 102 (1992); and Thalmeir et al., Blood 83: 1799 (1994)).

The ability to culture hematopoietic cells and their precursors (derived from the bone marrow, peripheral blood, or umbilical cord blood of a patient or donor) offers the potential to vastly improve immunosuppressive and immunodestructive protocols currently used in treating cancer and other life-threatening immune disorders. Ex vivo cultured hematopoietic cells, for example, may be used to reconstitute a patient's blood-clotting and infection-fighting functions following such therapies. Additionally, the ability to expand a desired population of hematopoietic cells in vitro would alleviate dependence on bone marrow aspiration and multiple aphereses as the only means of obtaining sufficient cell numbers for transplants.

Early work in the field of hematopoietic stem cell culture centered around the culture of murine bone marrow aspirates in agar gel or liquid medium. Unfractionated bone marrow (including stem cells, progenitor cells, more differentiated hematopoietic cells, and stromal elements) was used to inoculate the cultures, but they were generally short-lived and resulted in little or no increase in cell number, particularly in the stem cell and progenitor compartments. The results were even less promising when human bone marrow was employed. The human cells generally adhered to the bottom and sides of the culture vessel and their removal was difficult.

Subsequent efforts focused on inoculating mouse bone marrow onto pre-established monolayers of bone marrow stromal cells (so-called Dexter cultures; Dexter, Acta Haematol, 62:299–305, 1979). While some success was obtained with Dexter cultures of mouse cells, the same approach was disappointing with human cells, in that a steady decline in the numbers of all cell types is observed in human Dexter cultures (Quesenberry, Curr. Topics Microbiol. Immunol. 177: 151 (1992)).

A further disadvantage of Dexter cultures is that, to the extent that there is expansion of hematopoietic precursor cells, these cells adhere to the stromal layer and are extremely difficult to recover from the culture without employing conditions which damage the cells. The proliferating cells which are released into the culture medium (that is, the non-adherent cells) are generally more mature cells, which cannot restore sustained hematopoiesis in a transplanted individual.

According to the present invention, multiple stromal cell lines have been created which secrete a unique profile of human cytokines and which are useful for conditioning media to culture human hematopoietic cells independent of bone marrow stromal elements such that these hematopoietic cells expand in number and can be harvested under conditions which enhance the yield and recovery of hematopoietic precursor cells without compromising viability.

SUMMARY OF THE INVENTION

The present invention provides methods and compositions for sustaining and/or expanding the number of human hematopoietic precursor cells. In one embodiment the method for sustaining or expanding the human hematopoietic precursor cells includes inoculating the cells from a blood product, such as bone marrow, umbilical cord blood, or peripheral blood, into a culture vessel which contains a culture medium that has been conditioned by exposure to a human stromal cell line. Preferred human stromal cell lines used according to the methods of the present invention secrete one or more of the following interleukins (IL); IL-1, IL-1alpha, IL-1beta, IL-2, IL-3, IL-4, IL-5, IL-6, IL-7, IL-8, IL-10, IL-11, IL-12, IL-13, IL-14, IL-15, IL-16, IL-17, IL-18, or IL-19; or one or more of the following cytokines; FLT3L (Fms-like Tyrosine Kinase 3 Ligand), SCF (Stem Cell Factor), LIF (Leukemia Inhibitory Factor), M-CSF (Macrophage-Colony Stimulating Factor), TGF-beta 1 (Transforming Growth Factor-beta1), GM-CSF (Granulocyte-Colony Stimulating Factor), MCP-1 (Monocyte Chemotactic Protein-1), MIP-1alpha (Macrophage Inflammatory Protein-1alpha), G-CSF (Granulocyte-Colony Stimulating Factor), MCP-1 (Monocyte Chemotactic Protein-1), Tpo (Thrombopoietin), TNF-alpha (Tumor Necrosis Factor-alpha), or EPO (erythropoietin; U.S. Pat. No. 4,703,008, incorporated herein by reference). These cell lines may be irradiated and/or non-irradiated. Preferred cell lines used according to the methods of the invention include the human stromal cell lines designated HGS2.11, HGS2.52, HGS3.18, HGS3.30, HGS3.65, HGS3.66, HGS3.103, HGS3.114 which were deposited with the ATCC on Dec. 14, 1999 and assigned the following deposit numbers: HGS3.18 was assigned ATCC number PTA-1054, HGS3.66 was assigned ATCC number PTA-1055, HGS2.52 was assigned ATCC number PTA-1056, HGS3.103 was assigned ATCC number PTA-1057, HGS3.114 was assigned ATCC number PTA-1058, HGS2.11 was assigned ATCC number PTA-1059, HGS3.30 was assigned ATCC number PTA-1060, and HGS3.65 was assigned ATCC number PTA-1061. The cell lines referred to above have been directed to a biological deposit with the ATCC at 10801 University Boulevard, Manassas, Va. 20110-2209. The strains referred to are being maintained under the terms of the Budapest Treaty and will be made available to a patent office signatory to the Budapest Treaty. Additionally, all cell lines have been cultured and deposited in modified Dexter media (see Example 2; Dexter et al., J. Cell Physiology, 91:335 (1977)). These cells may easily be transferred to modified Whitlock-Witte media (see Example 2; Whitlock et al., Proc. Natl. Acad. Sci. USA, 79:3608 (1982)) by one of ordinary skill in the art. Note, however, that long-term propagation is preferably performed using modified Dexter media. In one embodiment, the conditioned culture medium compositions of the invention are supplemented with at least one exogenously added growth factor. Growth factors that may be used to supplement the conditioned culture medium compositions of the invention include, but are not limited to, one or more of the growth factors selected from the group consisting of: granulocyte colony stimulating factor, stem cell factor, and interleukin-3. In other non-exclusive embodiments, the conditioned culture medium compositions of the invention are supplemented with sera, such as, for example, animal sera. Animal sera that may be used to supplement the conditioned culture media of the invention, include, but are not limited to, one or more of the animal seras selected from the group consisting of: human sera, fetal bovine sera, calf, donor calf sera, and horse sera. The hematopoietic precursor cells are optionally separated from mature hematopoietic cells present initially in the blood product prior to inoculating the conditioned culture medium. Further, the separated hematopoietic precursor cells may be frozen initially for storage, and then thawed prior to inoculating the conditioned medium. Typically the cells will be cultured for a time and under conditions sufficient to achieve at least an approximately two- to five-fold expansion in the number of precursor cells relative to the number of cells present initially in the blood product. After the desired expansion or maintenance has taken place, the human hematopoietic precursor cells can then be harvested from the culture medium and returned to a patient, or frozen and stored.

In other embodiments, the invention provides compositions for sustaining or expanding the number of human hematopoietic precursor cells. In one embodiment, the compositions of the invention comprise a nutrient medium that has been conditioned by exposure to one or more of the immortalized human stromal cell lines of the invention. These immortalized human stromal cell lines may be irradiated and/or non-irradiated. In specific embodiments, the nutrient medium has been conditioned by exposure to one or more human stromal cell lines selected from the group consisting of HGS2.11, HGS2.52, HGS3.18, HGS3.30, HGS3.65, HGS3.66, HGS3.103, and HGS3.114. In one embodiment, the compositions of the invention are supplemented with at least one exogenously added growth factor. Growth factors that may be used to supplement the compositions of the invention include, but are not limited to, one or more of the growth factors selected from the group consisting of granulocyte colony stimulating factor, stem cell factor, and interleukin-3. In other non-exclusive embodiments, the compositions of the invention are supplemented with sera, such as, for example, animal sera. Animal sera that may be used to supplement the conditioned culture media of the invention, include, but are not limited to, one or more of the animal seras selected from the group consisting of human sera, fetal bovine sera, calf, donor calf sera, and horse sera.

In other embodiments the invention provides an immortalized human stromal cell line which sustains the proliferation of human hematopoietic precursor cells. These cell lines may be irradiated or non-irradiated. Preferred human stromal cell lines of the invention secrete one or more cytokines. In specific embodiments, the human stromal cell lines of the invention secrete one or more cytokines selected from the group consisting of: IL-7, IL-8, IL-11, FLT3L, SCF, LIF, M-CSF, TGF-beta 1, GM-CSF, MIP-1alpha, G-CSF, MCP-1, Tpo, IL-1alpha, IL-1beta, and TNF-alpha. In specific embodiments the immortalized human stromal cell line is a cell line selected from the group consisting of HGS2.11, HGS2.52, HGS3.18, HGS3.30, HGS3.65, HGS3.66, HGS3.103, and HGS3.114. In a preferred embodiment, the human stromal cell line is HGS2.11. In another preferred embodiment, the human stromal cell line is HGS3.18.

The immortalized human stromal cell lines of the invention can also be used as feeder layers in ex vivo bone marrow cultures or in colony forming assays, such as the methylcellulose assay for CFU-GM. Alternatively, the cell lines of the instant invention may be used to condition medium, which medium may then be used to sustain and/or expand ex vivo cultures of human hematopoietic precursor cells, or to sustain colony forming assays. In a further aspect of the invention, medium conditioned by exposure to the immortalized human stromal cell lines may also be used in vivo to promote hematopoiesis in patients whose bone marrow function is compromised.

DETAILED DESCRIPTION

The present invention provides compositions and methods for increasing the number of human hematopoietic precursor cells in vitro and in vivo. Specifically, the present invention provides immortalized human stromal cell lines that can be used as feeder layers to sustain the growth and differentiation of human hematopoietic precursor cells ex vivo. In another aspect, the immortalized human stromal cell lines of the present invention can be used to condition medium, which medium can be used in addition to or in lieu of a feeder cell layer and/or exogenously added growth factors or animal sera to support the growth of human hematopoietic precursor cells.

Human hematopoietic precursor cells are separated from a blood product, such as bone marrow, peripheral blood, or umbilical cord blood of a patient or donor, fetal peripheral blood and other sources. As discussed in more detail below, such separation may be performed, for example, by immunoselection on the basis of their expression of an antigen, such as the CD34 antigen, which is present on substantially all hematopoietic precursor cells, but is substantially absent from more mature hematopoietic cells. The separated hematopoietic precursor cells may be stored frozen and thawed at a later date for inoculation into a suitable vessel containing a culture medium comprising a conditioned medium and nutritive medium, optionally supplemented with a source of growth factors and, optionally, human or other animal plasma or serum. Alternatively, the separated cells may be inoculated directly into culture without first freezing. In both cases the resultant cell suspension is cultured under conditions and for a time sufficient to increase the number of hematopoietic precursor cells relative to the number of such cells present initially in the blood product. The cells may then be separated by any of a variety of methods, such as centrifugation or filtration, from the medium in which they have been cultured, and may be washed one or more times with fresh medium or buffer. Optionally, the cells may be re-separated into CD34-positive and -negative fractions, prior to resuspension to a desired concentration in a medium or buffer suitable for infusion. The cells may then be infused into a patient or stored frozen for infusion at a later date.

Surprisingly, separated precursor cells, such as CD34-positive cells, will expand in number when cultured in the presence of conditioned medium containing expressed products of bone marrow stromal elements, enabling clinically practicable expansion and recovery of hematopoietic precursor cells. By working with separated precursor cells, the volumes of cells and culture fluids which must be handled are reduced to more manageable numbers. Further, a high degree of expansion can be achieved when one starts with separated CD34-positive cells, rather than with an unseparated blood product. This is believed to be due to the removal of cells otherwise present in the blood product, which inhibit expansion of the precursor cells. Under the conditions employed in the methods of this invention, cell recovery is greatly facilitated and viability is preserved. Most importantly, the yield of hematopoietic precursor cells, capable of mediating both long-term and short-term hematopoietic recovery in a myelosuppressed or myeloablated host, is increased. The ability to sustain or expand hematopoietic precursor cells in vitro or in vivo by the compositions and methods of the present invention is expected to have tremendously important consequences for disease treatments which are inherently myelosuppressive or myeloablative, such as in cancer chemotherapy.

Within the context of the present invention, hematopoietic precursor cells include those cells which express the CD34 antigen, among other surface antigens, and include totipotent stem cells as well as committed progenitor cells. The level of expression of the CD34 antigen will vary from one cell type to another. Consequently, a cell is operationally defined as CD34-positive if it expresses sufficient CD34 antigen to be detected by a given method of assay. For example, CD34-positive cells can be identified by flow microfluorimetry using a fluorescence-activated cell sorter (FACS), by immunofluorescence or immunoperoxidase staining using a fluorescence or light microscope, by radioimmunoassay, or by immunoaffinity chromatography, among numerous other methods which will be readily apparent to one skilled in the art (see, for example, Lansdorp and Thomas (in Bone Marrow Processing and Purging, A. P. Gee (ed.), Boca Raton: CRC Press (1991) pg. 351). Hematopoietic precursor cells can also be detected by various colony-forming assays, such as CFU-GM and CFU-S assays (see, e.g., Sutherland et al., in Bone Marrow Processing and Purging, supra at p. 155).

In other embodiments the invention provides an immortalized human stromal cell line which sustains the proliferation of human hematopoietic precursor cells. This cell line may be irradiated or non-irradiated. Preferred human stromal cell lines of the invention secrete one or more cytokines. In specific embodiments, the human stromal cell lines of the invention secrete one or more cytokines selected from the group consisting of, but not limited to: IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, FLT3L, SCF, LIF, M-CSF, TGF-beta1, GM-CSF, MCP-1, MIP-1alpha, G-CSF, MCP-1, Tpo, TNF-alpha, and EPO. Included in the present invention are cell lines which secrete any combination of one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two or all of the above-mentioned cytokines. Further included are cell lines which do not secrete any one or combination of two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, or thirty-two of the above-mentioned cytokines. In a specific embodiment, the human stromal cell of the invention secretes IL-7, IL-8, IL-11, FLT3L, SCF, LIF, M-CSF, TGF-beta 1, GM-CSF, MIP-1alpha, G-CSF, and MCP-1. In another embodiment the human stromal cell of the invention secretes IL-7, IL-8, FLT3L, SCF, LIF, M-CSF, TGF-beta 1, GM-CSF, MIP-1alpha, G-CSF, and MCP-1. In another embodiment, the human stromal cell of the invention secretes IL-7, IL-8, FLT3L, SCF, LIF, M-CSF, MIP-1alpha, G-CSF, and MCP-1. In another embodiment, the human stromal cell of the invention secretes IL-7, IL-8, IL-11, FLT3L, SCF, LIF, M-CSF, MIP-1alpha, G-CSF, and MCP-1. In another embodiment, the human stromal cell of the invention secretes IL-7, IL-8, IL-11, FLT3L, SCF, LIF, M-CSF, GM-CSF, MIP-1alpha, G-CSF, and MCP-1. In another specific embodiment, the human stromal cell of the invention secretes IL-7, IL-8, IL-11, SCF, LIF, M-CSF, MIP-1alpha, G-CSF, and MCP-1. Also in a specific embodiment, the human stromal cell line of the invention does not secrete IL-11. In another embodiment, the human stromal cell of the invention does not secrete TGF-beta1. In another embodiment, the human stromal cell of the invention does not secrete GM-CSF. In another embodiment, the human stromal cell of the invention does not secrete IL-11, TGF-beta1, or GM-CSF. In another embodiment, the human stromal cell of the invention does not secrete FLT3L. In another embodiment, the human stromal cell of the invention does not secrete FLT3L, TGF-beta1, or GM-CSF. Therefore the present invention includes human stromal cell lines which either secrete or do not secrete any combination of cytokines including, but not limited to, those cited above. In specific embodiments the immortalized human stromal cell line of the invention is a cell line selected from the group consisting of HGS2.11, HGS2.52, HGS3.18, HGS3.30, HGS3.65, HGS3.66, HGS3.103, HGS3.114. In a preferred embodiment, the human stromal cell line is HGS2.11. In another preferred embodiment, the human stromal cell line is HGS3.18.

The above mentioned immortalized stromal cell lines were found to secrete cytokines as shown in Table 1 (see also Example 2). In Table 1, each row of the first column indicates which cytokine was tested for its presence in the media. Whether a human stromal cell line is deemed to secrete a particular cytokine is determined by the level of sensitivity of the assay as indicated for each cytokine in column 1 of Table 1 (see Example 2). Assay sensitivities are indicated as picograms/milliliter (pg/ml). In contrast, all secreted cytokine quantities are indicated (at a 1000 fold higher level) in nanograms/milliliter (ng/ml). A human stromal cell line that secretes a particular cytokine below the sensitivity levels listed in column 1, Table 1, is deemed not to secrete that cytokine for purposes of the present invention. Column two indicates the cytokine levels detected in Iscove's Modified Dulbecco's Medium (the base medium for modified Whitlock-Witte medium) before stromal cell conditioning. Column three indicates the cytokine level detected in Myelocult Medium (the base medium for modified Dexter medium) before stromal cell conditioning. Column four indicates the particular media condition used for each test. Columns 5 to 11 indicate the cell lines analyzed for cytokine secretion. Determination of whether a given stromal cell line secreted one or multiple cytokines was made under the conditions listed in Table 1 and disclosed in the Examples sections herein. For example, cytokine levels were determined after culturing the stromal cell lines in modified Dexter medium or modified Whitlock-Witte medium (see Examples). "<<sensitivity" indicates cytokine quantities below detectable levels for the corresponding cytokine assay (see Examples). "xxxxxxx" indicates data not available. "M/Whitlock-Witte" and "M/Whitlock-Witte IR" indicate non-irradiated or irradiated stromal cells, respectively, cultured in modified Whitlock-Witte medium. "M/Dexter" and "M/Dexter IR" indicate non-irradiated or irradiated stromal cells, respectively, cultured in modified Dexter medium. Standard deviations were derived from the results of duplicate samples. It is further noted that the cytokine levels indicated for each cell line in Table 1 are "net" cytokine concentrations which do not include exogenously added cytokines (in other words, values for cytokines added exogenously, via fresh media, have already been subtracted from the values shown for each cell-culture media after conditioning).

Preferred human stromal cell lines of the present invention secrete particular cytokines "at" levels listed in Table 1. Further preferred human stromal cell lines of the present invention secrete cytokines at levels "at least" or "greater than" the level listed in Table 1. In other embodiments, the human stromal cell lines of the invention secrete cytokines at detectable levels that are "at least" or "less than" the levels listed in Table 1. Further included in the present invention are cells lines that secrete cytokines "at least", "greater than", "at most" or "less than" the levels listed in Table 1 plus 3 times or minus 3 times the level of sensitivity for the particular cytokine. For example, included in the present invention are human stromal cell lines which secrete "50.96+1.7 pg/ml IL-8", "at least 50.96+1.7 pg/ml IL-8", "less than 50.96+1.7 pg/ml IL-8", 80.96+1.7 pg/ml IL-8" (10 pg/ml sensitivity×3+50.96+1.7 pg/ml), and/or "20.96+1.7 pg/ml IL-8" (10 pg/ml sensitivity×3−50.96+1.7 pg/ml).

The above levels of IL-8 are meant to exemplify not limit, since human stromal cell lines which secrete a particular cytokine of Table 1 "at", "at least", "greater than", "at most", or, "less than" any of the cytokine levels listed in Table 1 are include in the present invention, as are human stromal cell lines which produce a particular cytokine at the levels listed in Table 1+3× the sensitivity level or −3× the sensitivity level.

As discussed herein, the stromal cell lines of the invention may be irradiated. Subsequent to irradiation the cytokine profile for a given cell line may change. For example, following irradiation a stromal cell line may secrete more, less, or undetectable levels of a given cytokine as compared to the levels secreted by that cell line before irradiation. Thus, following irradiation a stromal cell line may secrete a new cytokine not previously found in detectable quantities. Stromal cell irradiation may optionally be performed to halt cell proliferation (without killing the cells) in order to perform cobblestone assays (see Example 3).

In a specific embodiment of the invention, stromal cell irradiation is performed as follows: cells are seeded into the appropriate dishes or plates and cultured until reaching ~95% confluence. The cells are then placed in a 137Cs irradiator (J. L. Shepard & Associates Model Mark 1-68A irradiator) and subjected to a 15 Gray (1500 Rads) dose of radiation. The cell media is immediately removed and replaced with fresh media.

To assess the ability of stromal cells to support hematopoiesis, cobblestone area forming assays may be performed using techniques known in the art, or as described in Example 3. Briefly, in one embodiment cobblestone area forming assays may be performed by seeding stromal cell lines in dishes or wells of plates and growing to confluence. The cell plates are then irradiated to prevent further mitosis. The media is then replaced with fresh media and hematopoietic cells are seeded onto the stromal cell monolayers and incubated at 37° C. in 5% $CO_2$. The cultures are subsequently monitored weekly for the appearance and/or disappearance of cobblestone areas (Table 2 discloses data generated using this assay, as described in Example 3). Appearance of cobblestone areas is indicative of hematopoietic cell growth and proliferation. Half media replacement was performed weekly.

TABLE 1

| Cytokine | Iscove's* | Myelocult** | Conditions | HGS2.11 | HGS2.52 | HGS3.18 | HGS3.30 | HGS3.65 | HGS3.66 | HGS3.103 | HGS3.114 |
|---|---|---|---|---|---|---|---|---|---|---|---|
| IL-7 pg/ml Sensitivity <0.1 pg/ml | 0.14 ± 0.005 | 0.12 ± 0.009 | M/Whitlock-Witte | xxxxxxx | xxxxxxx | 4.70 ± 0.00 | xxxxxxx | xxxxxxx | 3.58 ± 0.33 | 2.70 ± 0.80 | 5.30 ± 0.22 |
| | | | M/Whitlock-Witte IR | xxxxxxx | xxxxxxx | 3.04 ± 0.00 | xxxxxxx | xxxxxxx | 3.10 ± 0.10 | 2.10 ± 0.50 | 3.90 ± 0.06 |
| | | | M/Dexter | 2.42 ± 0.16 | 17.84 ± 0.11 | 1.70 ± 0.00 | 2.35 ± 0.10 | 5.83 ± 0.63 | 4.72 ± 0.52 | 3.40 ± 0.30 | 4.00 ± 0.10 |
| | | | M/Dexter IR | 2.64 ± 0.37 | 13.84 ± 0.9 | 1.08 ± 0.40 | 1.53 ± 0.03 | 3.85 ± 0.09 | 3.58 ± 0.80 | 2.55 ± 0.33 | 2.90 ± 0.06 |
| IL-8 ng/ml Sensitivity <10 pg/ml | <<sensitivity | <<sensitivity | M/Whitlock-Witte | xxxxxxx | xxxxxxx | 7.88 ± 3.3 | xxxxxxx | xxxxxxx | <<sensitivity | <<sensitivity | <<sensitivity |
| | | | M/Whitlock-Witte IR | xxxxxxx | xxxxxxx | 10.80 ± 0.4 | xxxxxxx | xxxxxxx | <<sensitivity | <<sensitivity | <<sensitivity |
| | | | M/Dexter | 36.255 ± 0.67 | 39.7 ± 1.65 | 32.63 ± 0.6 | 33.75 ± 1.04 | 31.44 ± 1.09 | 39.01 ± 1.3 | 38.39 ± 2.0 | 28.62 ± 2.4 |
| | | | M/Dexter IR | 51.11 ± 2.16 | 80.36 ± 1.43 | 40.53 ± 1.2 | 27.87 ± 0.54 | 48.93 ± 0.27 | 63.88 ± 0.08 | 53.79 ± 1.9 | 38.20 ± 2.6 |
| IL-11 pg/ml Sensitivity <8 pg/ml | 43.24 ± 2.54 | 36.73 ± 4.12 | M/Whitlock-Witte | xxxxxxx | xxxxxxx | <<sensitivity | xxxxxxx | xxxxxxx | 31.65 ± 0.32 | <<sensitivity | <<sensitivity |
| | | | M/Whitlock-Witte IR | xxxxxxx | xxxxxxx | <<sensitivity | xxxxxxx | xxxxxxx | 56.57 ± 8.25 | <<sensitivity | <<sensitivity |
| | | | M/Dexter | 39.43 ± 0 | 8.67 ± 1.0 | <<sensitivity | <<sensitivity | <<sensitivity | 211.9 ± 7.62 | <<sensitivity | <<sensitivity |
| | | | M/Dexter IR | 76.23 ± 0 | 41.53 ± 1.07 | <<sensitivity | 12.35 ± 2.60 | <<sensitivity | 349.04 ± 5.08 | <<sensitivity | <<sensitivity |
| FLT3L pg/ml Sensitivity <7 pg/ml | <<sensitivity | <<sensitivity | M/Whitlock-Witte | xxxxxxx | xxxxxxx | 7.99 ± 0.27 | xxxxxxx | xxxxxxx | 9.55 ± 0.49 | <<sensitivity | 10.60 ± 0.28 |
| | | | M/Whitlock-Witte IR | xxxxxxx | xxxxxxx | 6.94 ± 0.24 | xxxxxxx | xxxxxxx | 10.54 ± 0.49 | <<sensitivity | 9.80 ± 0.28 |
| | | | M/Dexter | <<sensitivity | 34.55 ± 0.8 | <<sensitivity | <<sensitivity | 12.13 ± 1.06 | 8.16 ± 0.00 | 10.07 ± 0.25 | 7.38 ± 0.86 |
| | | | M/Dexter IR | <<sensitivity | 36.25 ± 1.06 | <<sensitivity | 7.60 ± 0.53 | 15.89 ± 1.06 | 7.12 ± 0.49 | 11.11 ± 0.25 | 8.60 ± 0.28 |
| SCF pg/ml Sensitivity <9 pg/ml | <<sensitivity | <<sensitivity | M/Whitlock-Witte | xxxxxxx | xxxxxxx | 125.59 ± 1.14 | xxxxxxx | xxxxxxx | 95.77 ± 9.12 | 140.90 ± 1.14 | 153.3 ± 8.5 |
| | | | M/Whitlock-Witte IR | xxxxxxx | xxxxxxx | 110.28 ± 1.14 | xxxxxxx | xxxxxxx | 108.26 ± 3.99 | 124.78 ± 3.42 | 159.98 ± 5.39 |
| | | | M/Dexter | 64.62 ± 0 | 235.622 ± 7.19 | 131.23 ± 3.42 | 157.75 ± 11.24 | 249.29 ± 17.53 | 98.99 ± 2.28 | 320.24 ± 6.27 | 1.6.58 ± 8.9 |
| | | | M/Dexter IR | 67.16 ± 0 | 214.64 ± 0.89 | 90.13 ± 2.28 | 136.773 ± 2.24 | 255.964 ± 8.09 | 70.78 ± 0.0 | 263.82 ± 8.55 | 111.66 ± 4.45 |
| LIF pg/ml Sensitivity <8 pg/ml | <<sensitivity | <<sensitivity | M/Whitlock-Witte | xxxxxxx | xxxxxxx | 146.73 ± 6.30 | xxxxxxx | xxxxxxx | 9.26 ± 2.5 | 84.02 ± 2.52 | 26.610 ± 0.63 |
| | | | M/Whitlock-Witte IR | xxxxxxx | xxxxxxx | 222.42 ± 20.77 | xxxxxxx | xxxxxxx | 43.97 ± 3.7 | 131.20 ± 5.03 | 43.52 ± 0.63 |
| | | | M/Dexter | 63.55 ± 1.59 | 121.41 ± 3.77 | 162.35 ± 3.78 | 109.39 ± 0.63 | 151.69 ± 112.59 | 322.12 ± 20.70 | 294.52 ± 9.44 | 167.69 ± 6.3 |

TABLE 1-continued

| Cytokine | Iscove's* | Myelocult** | Conditions | HGS2.11 | HGS2.52 | HGS3.18 | HGS3.30 | HGS3.65 | HGS3.66 | HGS3.103 | HGS3.114 |
|---|---|---|---|---|---|---|---|---|---|---|---|
| | | | M/Dexter IR | 74.68 ± 4.41 | 372.85 ± 6.30 | 162.34 ± 2.52 | 109.39 ± 0.63 | 191.27 ± 10.69 | 3333.24 ± 2.52 | 330.13 ± 10.69 | 162.79 ± 5.66 |
| M-CSF pg/ml Sensitivity <9 pg/ml | <<sensitivity | <<sensitivity | M/Whitlock-Witte | xxxxxxx | xxxxxxx | 1121.08 ± 10.97 | xxxxxxx | xxxxxxx | 1235.06 ± 51.2 | 1233.16 ± 1.22 | 1225.40 ± 46.33 |
| | | | M/Whitlock-Witte IR | xxxxxxx | xxxxxxx | 1090.04 ± 10.97 | xxxxxxx | xxxxxxx | 1492.99 ± 17.1 | 1183.16 ± 20.73 | 1124.53 ± 57.31 |
| | | | M/Dexter | 1692.68 ± 285.31 | 6510.55 ± 478.14 | 565.85 ± 42.67 | 911.57 ± 114.61 | 1705.63 ± 1.22 | 2544.86 ± 79.79 | 1559.92 ± 39.02 | 1127.12 ± 46.33 |
| | | | M/Dexter IR | 1724.59 ± 218.25 | 7111.45 ± 968.94 | 583.09 ± 42.67 | 720.17 ± 53.65 | 1798.74 ± 128.03 | 2290.96 | 1596.99 ± 25.61 | 1073.66 ± 43.89 |
| TGF-β1 pg/ml Sensitivity <7 pg/ml | 990.76 ± 38.82 | 2510.70 ± 100.63 | M/Whitlock-Witte | xxxxxxx | xxxxxxx | 1945.88 ± 696.54 | xxxxxxx | xxxxxxx | 2234.71 ± 382.99 | 2293.36 ± 528.52 | 2312.74 ± 38.25 |
| | | | M/Whitlock-Witte IR | xxxxxxx | xxxxxxx | 1800.04 ± 400.78 | xxxxxxx | xxxxxxx | 2105.52 ± 346.42 | 1936.65 ± 355.80 | 2396.76 ± 263.87 |
| | | | M/Dexter | | | 581.51 ± 485.77 | | | 1493.13 ± 414.80 | 1392.99 ± 280.35 | 876.83 ± 263.87 |
| | | | M/Dexter IR | | | 456.59 ± 278.49 | | | 1979.02 ± 219.98 | 1598.42 ± 30.495 | 768.28 ± 366.25 |
| GM-CSF pg/ml sensitivity >1 pg/ml | <<sensitivity | <<sensitivity | M/Whitlock-Witte | xxxxxxx | xxxxxxx | 7.518 ± 0.19 | xxxxxxx | xxxxxxx | 3.86 ± 2.31 | 2.63 ± 0.72 | <<sensitivity |
| | | | M/Whitlock-Witte IR | xxxxxxx | xxxxxxx | 10.23 ± 0.62 | xxxxxxx | xxxxxxx | 8.58 ± 1.5 | 3.2 ± 0.58 | <<sensitivity |
| | | | M/Dexter | <<sensitivity | <<sensitivity | 19.725 ± 2.69 | <<sensitivity | <<sensitivity | 16.37 ± 1.74 | 7.13 ± 0.82 | 1.758 ± |
| | | | M/Dexter IR | <<sensitivity | 1.24 ± 0.32 | 25.31 ± 0.61 | <<sensitivity | <<sensitivity | 22.00 ± 1.59 | 11.65 ± 0.25 | 3 ± |
| MIP-1α pg/ml sensitivity >7 pg/ml | 4.24 ± 0.0 | 20.62 ± 0.07 | M/Whitlock-Witte | xxxxxxx | xxxxxxx | 49.44 ± 2.17 | xxxxxxx | xxxxxxx | 7.21 ± 1.44 | 8.98 ± 1.05 | 6.97 ± 0.36 |
| | | | M/Whitlock-Witte IR | xxxxxxx | xxxxxxx | 87.74 ± 2.03 | xxxxxxx | xxxxxxx | 37.35 ± 2.25 | 19.87 ± 0 | 11.89 ± 1.00 |
| | | | M/Dexter | 264.15 ± 3.25 | 55.37 ± 0.98 | 59.62 ± 2.99 | 30.75 ± 1.93 | 44.79 ± 2.93 | 25.91 ± 2.49 | 34.03 ± 1.89 | 53.25 ± 4.66 |
| | | | M/Dexter IR | 347.016 ± 40.36 | 92.89 ± 4.56 | 100.42 ± 1.49 | 50.31 ± 6.84 | 133.407 ± 1.30 | 44.76 ± 2.11 | 54.18 ± 2.33 | 64.53 ± 4.59 |
| G-CSF pg/ml sensitivity >0.4 pg/ml | <<sensitivity | <<sensitivity | M/Whitlock-Witte | xxxxxxx | xxxxxxx | 33.3 ± 3.15 | xxxxxxx | xxxxxxx | <sensitivity | 4.11 ± 0.24 | <<sensitivity |
| | | | M/Whitlock-Witte IR | xxxxxxx | xxxxxxx | 46.65 ± 3.25 | xxxxxxx | xxxxxxx | 1.01 ± 0.04 | 5.39 ± 0.11 | 0.503 ± 0.07 |
| | | | M/Dexter | 1849.2 ± 83.2 | 7.15 ± 3 | 491.05 ± 6.7 | 218.5 ± 2.3 | 72.75 ± 2.2 | 29.55 ± 1.75 | 252.55 ± 0.9 | 96.7 ± 8.35 |
| | | | M/Dexter IR | 2331.9 ± 140.2 | 59.9 ± 3.9 | 635.25 ± 12.1 | 182.05 ± 7.2 | 103.1 ± 7.2 | 50.25 ± 2.9 | 384.75 ± 0.4 | 110.2 ± 49.1 |
| Tpo pg/ml sensitivity >15 pg/ml | <<sensitivity | 71.4141 ± 10.80 | <<sensitivity <<sensitivity <<sensitivity <<sensitivity | xxxxxxx xxxxxxx <<sensitivity <<sensitivity | xxxxxxx xxxxxxx <<sensitivity <<sensitivity | <<sensitivity <<sensitivity <<sensitivity <<sensitivity | xxxxxxx xxxxxxx <<sensitivity <<sensitivity | xxxxxxx xxxxxxx <<sensitivity <<sensitivity | <<sensitivity <<sensitivity <<sensitivity <<sensitivity | <<sensitivity <<sensitivity <<sensitivity <<sensitivity | <<sensitivity <<sensitivity <<sensitivity <<sensitivity |
| MCP-1 ng/ml sensitivity 5.0 pg/ml | <<sensitivity | 8.622 ± 0.0 | M/Whitlock-Witte | xxxxxxx | xxxxxxx | 9.62 ± 0.11 | xxxxxxx | xxxxxxx | 5.92 ± 0.11 | 9.94 ± 0.34 | 3.64 ± 0.11 |
| | | | M/Whitlock-Witte IR | xxxxxxx | xxxxxxx | 10.55 ± 0.69 | xxxxxxx | xxxxxxx | 8.28 ± 0.27 | 10.62 ± 0.44 | 4.67 ± 0.41 |
| | | | M/Dexter | 8.04 ± 0.29 | 16.26 ± 0.05 | 7.08 ± 0.71 | 12.16 ± 0.9 | 19.57 ± 0.0 | 27.05 ± 2.06 | 16.39 ± 0.25 | 7.80 ± 0.04 |
| | | | M/Dexter IR | 9.11 ± 0.05 | 23.15 ± 1.51 | 6.41 ± 0.37 | 13.61 ± 0.14 | 25.80 ± 1.11 | 27.47 ± 2.04 | 15.89 ± 0.77 | 6.91 ± 0.24 |
| IL-1α pg/ml sensitivity 0.5 pg/ml | <<sensitivity | <<sensitivity | M/Whitlock-Witte | xxxxxxx | xxxxxxx | <<sensitivity | xxxxxxx | xxxxxxx | <<sensitivity | <<sensitivity | <<sensitivity |
| | | | M/Whitlock-Witte IR | xxxxxxx | xxxxxxx | <<sensitivity | xxxxxxx | xxxxxxx | <<sensitivity | <<sensitivity | <<sensitivity |
| | | | M/Dexter | <<sensitivity | <<sensitivity | <<sensitivity | <<sensitivity | <<sensitivity | <<sensitivity | <<sensitivity | <<sensitivity |
| | | | M/Dexter IR | <<sensitivity | <<sensitivity | <<sensitivity | <<sensitivity | <<sensitivity | <<sensitivity | <<sensitivity | <<sensitivity |
| IL-1β pg/ml sensitivity 3.0 pg/ml | <<sensitivity | <<sensitivity | M/Whitlock-Witte | xxxxxxx | xxxxxxx | <<sensitivity | xxxxxxx | xxxxxxx | <<sensitivity | <<sensitivity | <<sensitivity |
| | | | M/Whitlock-Witte IR | xxxxxxx | xxxxxxx | <<sensitivity | xxxxxxx | xxxxxxx | <<sensitivity | <<sensitivity | <<sensitivity |
| | | | M/Dexter | <<sensitivity | <<sensitivity | <<sensitivity | <<sensitivity | <<sensitivity | <<sensitivity | <<sensitivity | <<sensitivity |
| | | | M/Dexter IR | <<sensitivity | <<sensitivity | <<sensitivity | <<sensitivity | <<sensitivity | <<sensitivity | <<sensitivity | <<sensitivity |
| TNF-α pg/ml sensitivity | <<sensitivity | <<sensitivity | M/Whitlock-Witte | xxxxxxx | xxxxxxx | <<sensitivity | xxxxxxx | xxxxxxx | <<sensitivity | <<sensitivity | <<sensitivity |
| | | | M/Whitlock-Witte IR | xxxxxxx | xxxxxxx | <<sensitivity | xxxxxxx | xxxxxxx | <<sensitivity | <<sensitivity | <<sensitivity |

TABLE 1-continued

| Cytokine | Iscove's* | Myelocult** | Conditions | HGS2.11 | HGS2.52 | HGS3.18 | HGS3.30 | HGS3.65 | HGS3.66 | HGS3.103 | HGS3.114 |
|---|---|---|---|---|---|---|---|---|---|---|---|
| 0.5 pg/ml | | | M/Dexter | <<sensitivity | <<sensitivity | <<sensitivity | <<sensitivity | <<sensitivity | <<sensitivity | <<sensitivity | <<sensitivity |
| | | | M/Dexter IR | <<sensitivity | <<sensitivity | <<sensitivity | <<sensitivity | <<sensitivity | <<sensitivity | <<sensitivity | <<sensitivity |

*Iscove's Modified Dulbecco's Medium (Life Technologies-Gibco BRL, Gaithersburg, MD, U.S.A.)
**Myelocult H5100 Medium (Stem Cell Technologies, Vancouver, BC, Canada)

TABLE 2

Cobblestone Area Forming Assay

| Cell Line | Week 2 | Week 3 | Week 4 | Week 5 | Week 6 |
|---|---|---|---|---|---|
| HGS2.11 | +/+ | +/+ | +/+ | +/sf | nd/nd |
| HGS2.52 | sf/sf | +/+ | +/+ | +/+ | +/+ |
| HGS3.18 | +/+ | +/+ | +/+ | +/+ | +/+ |
| HGS3.30 | +/+ | +/+ | +/+ | +/+ | nd/nd |
| HGS3.65 | nd/nd | +/+ | +/+ | +/+ | +/+ |
| HGS3.66 | sf/sf | +/+ | +/+ | +/+ | nd/nd |
| HGS3.103 | sf/sf | +/+ | +/+ | +/nd | nd/nd |
| HGS3.114 | nd/nd | +/+ | +/+ | sf/sf | nd/nd |

"+" indicates presence of cobblestone areas
"−" indicates no significant number of cobblestone areas observed
"sf" indicates a few, small cobblestone areas observed
"nd" indicates no data Hematopoietic precursor cells may be obtained from any of a variety of blood products, including bone marrow, peripheral blood, umbilical cord blood, fetal liver, and spleen. Bone marrow is a particularly rich source of precursor cells (1–2% of marrow), but alternate sources may be preferable because of the discomfort associated with bone marrow aspiration. Bone marrow is typically aspirated from the iliac crest, but may be obtained from other sites (such as the sternum or vertebral bodies) if necessitated by prior or concurrent disease or therapy.

Peripheral blood contains fewer precursor cells (typically<1% of peripheral blood mononuclear cells), but is generally easier to obtain than bone marrow. The number of precursor cells circulating in peripheral blood can be increased by prior exposure of the donor to certain growth factors, such as, for example, G-CSF or SCF (KL), and/or certain drugs, such as, for example, 5-fluorouracil, cyclophosphamide or prednisone (Korbling and Martin, Plasma Ther. Transfer Technol. 9:119 (1980)). Peripheral blood collected from patients or donors who have been pretreated to increase the number of circulating CD34-positive cells is referred to as having been "mobilized." Depending upon the volume which is desired, blood may be obtained by venipuncture or by one or more aphereses, for example, on a COBE 2997 blood separator. Precursor cells can also be obtained from umbilical cord blood at the time of delivery, either by simple gravity-induced drainage or manual expression as described in U.S. Pat. No. 5,004,681, incorporated herein by reference.

Although one can readily separate a bone marrow or peripheral blood specimen or apheresis product into precursor and mature cells, (such as CD34-positive and CD34-negative populations), it is generally preferred to prepare a buffy coat or mononuclear cell fraction from these specimens first, prior to separation into the respective populations. Methods for the preparation of buffy coats and mononuclear cell fractions are well-known in the art (Kumar and Lykke, Pathology 16:53 (1984)).

Separation of precursor cells from more mature cells can be accomplished by any of a variety of methods known to those skilled in the art, including, but not limited to, immunoaffinity chromatography (Basch et al., J. Immunol. Methods 56:269 (1983)), fluorescence-activated cell sorting, panning (Wysocki and Sato, Proc. Natl. Acad. Sci. USA 15: 2844 (1978)), magnetic-activated cell sorting (Miltenyi et al., Cytometry 11: 231 (1990)), and cytolysis. Generally, separation of a heterogeneous population of cells, such as in a bone marrow aspirate or a peripheral blood specimen or apheresis product, into target (such as, CD34-positive) and non-target (such as, CD34-negative) fractions is rarely complete. For the purposes of the present invention, separation is considered to have been accomplished if the target fraction is comprised of at least about 20% precursor cells, at least about 50% precursor cells, and preferably at least about 70% precursor cells. In addition, it may be desirable to keep the total numbers of mature hematopoietic cells, such as platelets, granulocytes, and red cells, as low as possible in order to prevent clumping and the release of degradative enzymes which can adversely affect the recovery and viability of engrafting cells, especially after freezing and thawing. More specifically, it may be desirable that the target fraction be comprised of less than about 5% platelets, 50% granulocytes, and 10% red cells and, preferably, less than about 1% platelets, 25% granulocytes, and 1% red cells.

Precursor cells may be positively selected or negatively selected. By positive selection is meant the capture of cells by some means, usually immunological, on the basis of their expression of a specific characteristic or set of characteristics (usually an antigen(s) expressed at the cell surface). For example, CD34-positive cells can be positively selected by any of the above methods (except cytolysis, which would result in destruction of the desired cells) on the basis of their expression of the CD34 antigen utilizing an anti-CD34 antibody, such as the monoclonal antibodies 12.8, My-10, and 8G12 (commercially available from Becton Dickinson Co., Mountain View, Calif.), or Q-Bend 10 (commercially available from Biosystems Ltd., Waterbeach, Cambridge, England).

Negative selection means the exclusion or depletion of cells by some means, usually immunological, on the basis of their lack of expression of a specific characteristic or set of characteristics (again, usually a surface antigen). For example, CD34-positive cells can be negatively selected by any of the above methods on the basis of their lack of expression of lineage-defining antigens, such as CD 19 (for B lymphocytes), CD3 (for T lymphocytes), CD56 (for NK cells), etc., utilizing antibodies to the above-mentioned and other lineage-defining antigens. By using a cocktail or mixture of monoclonal antibodies directed to red cell, platelet, granulocyte, lymphocyte and/or tumor cell antigens, it is possible to leave behind a population of cells which is highly enriched for CD34-positive cells. Numerous monoclonal and polyclonal antibodies suitable for this purpose are known in the art (see Leukocyte Typing IV, Knopp et al. (eds.), Oxford UP, 1989) and are commercially available from a wide variety of sources (for example, Becton Dickinson Co., Mountain View, Calif.; Coulter Immunology, Hialeah, Fla.; Ortho Diagnostics, Raritan, N.J., etc.).

Alternatively, precursor cells can be separated from mature cells by a combination of negative and positive selection techniques. A preferred combination of negative and positive selection techniques is comprised of a first selection for CD34-positive cells utilizing an anti-CD34 antibody, followed by a second selection for HLA-DR-negative/CD34-positive cells, using an anti-HLA-DR antibody to a non-polymorphic determinant on the DR molecule. Antibodies to non-polymorphic determinants on the HLA-DR molecules are well-known in the literature (see Knopp et al., supra) and are available from a variety of sources, including those mentioned above. An example of a suitable monoclonal anti-HLA-DR antibody is the antibody produced by the hybrid cell line L243 (Lampson et al., J. Immunol. 125: 293 (1980)), which cell line is available from the American Type Culture Collection (Rockville, Md.) under the designation ATCC HB55. The advantage of this or other dual selection strategies is that the volume of cells which is placed into culture is smaller and thus more manageable.

Although selection of CD34-positive cells usually involves the use of one or more antibodies or fragments thereof, in some cases selection may involve the use of lectins or other types of receptors or ligands expressed on the cell surface. Among other antibodies, antigens, receptors and ligands which may be useful, alone or in combination with other markers, for separating CD34-positive cells from CD34-negative cells are transferrin, the transferrin receptor, soybean agglutinin, c-kit ligand, c-kit receptor, HLA-DR, CD33, etc.

Within another aspect of the invention, the precursor cells are periodically separated from more mature cells. Briefly, mature cells (which include not only terminally differentiated blood cells, but cells of an intermediate lineage) may inhibit the expansion and differentiation of precursor cells via a feedback control mechanism. Removal of more mature cells from a culture thus permits expansion of the precursor cells to many times their original numbers. Within the context of the present invention, "periodically separating" means removal of mature cells at least every 7 days, preferably every 4 days.

Various methods may be utilized in order to periodically separate precursor from mature cells. For example, cells can be separated on an affinity column, incubated in a selected medium, and then subsequently reseparated in order to separate the precursor cells from the newly differentiated mature cells. Particularly preferred methods and devices for the selection of precursor cells, such as CD34-positive cells, are described in U.S. Pat. Nos. 5,215,927, 5,225,353, 5,262,334 and 5,240,856, each of which is incorporated herein by reference in its entirety. These applications describe methods and devices for isolating or separating target cells, such as hematopoietic precursor cells, from a mixture of non-target and target cells, wherein the target cells are labeled, directly or indirectly, with a biotinylated antibody to a target cell surface antigen. Labeled cells are separated from unlabeled cells by, flowing them through a bed of immobilized avidin, the labeled cells binding to the avidin by virtue of the biotinylated antibody bound to their surface, while the unlabeled cells pass through the bed. After washing the bed material, the labeled (bound) cells can be eluted from the bed, for example, by mechanical agitation. A cell separator device is also provided for separating target cells from non-target cells, comprising (a) a column assembly which includes a column, a sample fluid supply bag and a fluid collection bag wherein the column is provided for receiving the sample fluid from the sample fluid supply bag and for separating the target cells from the sample fluid and retaining the target cells, and wherein the fluid collection bag is provided for receiving the target cells after being released from the column, (b) an agitation means for agitating the contents of the column to assist in releasing the sample cells retained in the column, the agitation means being responsive to a drive signal for varying amounts of agitation of the contents of the column to vary the rate at which the sample cells are released, (c) a column sensor means for providing a column signal indicative of the optical density of fluid flowing out of the column and into the fluid collection bag, (d) a column valve means responsive to a column valve control signal for selectively enabling the fluid coming out of the column to flow into the fluid collection bag, and (e) a data processor means for controlling the operation of the cell separator, the data processor means being responsive to the column signal for providing the drive signal and the column valve control signal to prevent inadequate concentrations of the target cells from being collected.

Subsequent to separation, precursor cells are inoculated into a culture medium comprised of a nutritive medium, any number of which, such as RPMI, TC 199, Ex Vivo-10, or Iscove's DMEM, along with a source of growth factors, will be apparent to one skilled in the art. Proliferation and differentiation of precursor cells may be enhanced by the addition of various components to the medium, including a source of plasma or serum. Among sources of plasma or serum are fetal bovine and human. Particularly preferred are human autologous plasma or human ABO plasma which have been screened in accordance with standard blood bank procedures to ensure the absence of infectious agents, such as HBV or HIV. The amount of plasma or serum which is used will vary, but is usually between about 1 and 50% (by volume) of the medium in which the cells are grown, and more often between about 1 and 25%.

According to one aspect of the present invention, separated precursor cells are cultured in a nutritive medium containing a source of plasma or serum, which medium has been previously conditioned by exposure to immortalized stromal cells for a variable period of time and under conditions sufficient to allow those cells to secrete products, such as growth factors, into the medium. For example, conditioned medium suitable for the culture of separated CD34-positive cells may be prepared by inoculating an immortalized stromal cell line of the invention into a nutrient medium (optionally containing plasma or serum), allowing the cells to grow, usually for 1 to 3 days, and then separating the cells from the medium (for example, by centrifugation or filtration). Optionally, the conditioned medium may be sterilized and/or concentrated prior to use and/or supplemented by the addition of exogenous growth factors. In a specific embodiment, the conditioned media is prepared by inoculating one, two, three, four, five or more irradiated and/or non-irradiated immortalized stromal cell lines selected from the group consisting of: HGS2.11, HGS2.52, HGS3.18, HGS3.30, HGS3.65, HGS3.66, HGS3.103, and HGS3.114. In other non-exclusive embodiments, one or more of these stromal cell lines is irradiated. In a specific embodiment, the conditioned media is prepared by inoculating the stromal cell line HGS2.11. In another specific embodiment, the conditioned media is prepared by inoculating the stromal cell line HGS3.18.

The stromal cell lines of the invention secrete a unique profile of growth factors useful to prepare conditioned media for short term or long term culture of hematopoietic cells. Typically, such cell lines are prepared by transfecting a long term marrow culture with a retroviral supernatant, the retrovirus carrying an oncogene, integration of which leads to immortalization of the transfected cell and its progeny. The retroviral vector may also carry a gene for a selectable marker, such as neomycin resistance, to facilitate identification of transfected cells. Following transfection, cells are cloned and characterized morphologically and histochemically, as well as functionally to ascertain their ability to sustain hematopoiesis ex vivo. Growth factors expressed by the resultant cell lines can be assayed, for example, by ELISA or RIA.

In addition, it will be apparent that in some instances it may be desirable to inoculate multiple cell lines simultaneously to produce medium conditioned by more than one line. Alternatively, different batches of medium can be conditioned by different cell lines and the batches combined, after the cells have been separated and discarded, to achieve the same effect.

The length of time for which medium is conditioned may vary from 1 day to 2 weeks, but will usually be between 1 day and 1 week and more often, between 1 day and 5 days. In one embodiment the medium is condition for 48 hours before removing it from the cells. In addition to conditioning the medium by exposing it to irradiated and/or non-irradiated immortalized stromal cell lines of the invention, such as, for example, HGS2.11, HGS2.52, HGS3.18, HGS3.30, HGS3.65, HGS3.66, HGS3.103, and/or HGS3.114, the medium may also be supplemented by the addition of one or more purified or partially purified growth factors. In one embodiment, the compositions of the invention are supplemented with at least one, two, three, four, five, or more exogenously added growth factors. Growth factors that may be used to supplement the compositions of the invention include, but are not limited to, one or more of the growth factors selected from the group consisting of: granulocyte colony stimulating factor, stem cell factor, and interleukin-3. Additionally, the medium may be supplemented by addition of one or more sera, such as, for example, an animal sera. Animal sera that may be used to supplement the conditioned culture media of the invention, include, but are not limited to, one or more of the animal seras selected from the group consisting of: human sera, fetal bovine sera, calf, donor calf sera, and horse sera. As used herein, the term "conditioned medium" is used to include medium conditioned solely by exposure to cells as well as medium conditioned by exposure to cells and supplemented with exogenous growth factors and/or one or more sera.

Conditioned medium may be prepared with or without a source of serum or plasma. If used, the serum or plasma may be of human or other animal origin. Particularly preferred is human autologous plasma or human ABO plasma which has been screened in accordance with standard blood bank procedures to ensure the absence of infectious agents. The amount of plasma or serum which is used will vary, but is usually between about 1 and 50% (by volume) of the medium in which the cells are grown, and more often between about 1 and 25%.

The conditioned medium of the present invention may be concentrated prior to use by a variety of means, for example, by ultrafiltration, although other concentrating means known in the art will also suffice. The amount of concentration will vary, but is usually between 2 and 100-fold, more often between 2 and 50-fold, and most often between 2 and 10-fold. Separated precursor cells may be inoculated directly into conditioned medium (concentrated or non-concentrated) or they may be inoculated into a mixture of conditioned (concentrated or non-concentrated) and non-conditioned medium (with or without exogenously supplied growth factors and serum or plasma). If inoculated into a mixture of conditioned and non-conditioned medium, the ratio of conditioned (non-concentrated) to nonconditioned medium will usually be between 1:1 and 1:10 (on a volume basis), more often between 1:1 and 1:5, and most often between 1:1 and 1:2. Although these ratios are expressed for non-concentrated conditioned medium, it will be apparent to those skilled in the art that the equivalent ratios can be obtained using smaller volumes of concentrated conditioned medium.

Among growth factors which may be advantageously employed in the medium include, but are not limited to, any one or more of the growth factors selected from the group consisting of: interleukins (IL) 1–19, erythropoietin (EPO; U.S. Pat. No. 4,703,008, incorporated herein by reference), stem cell factor (SCF, also known as mast cell growth factor and c-kit ligand), granulocyte colony stimulating factor (G-CSF), granulocyte, macrophage-colony stimulating factor (GM-CSF), macrophage-colony stimulating factor (M-CSF), transforming growth factor beta (TGF beta), tumor necrosis factor alpha (TNF alpha), the interferons (IFN alpha, beta, or gamma), fibroblast growth factor (FGF), Fms-like Tyrosine Kinase 3 Ligand (FLT3L), Leukemia Inhibitory Factor (LIF), Macrophage Inflammatory protein (MIP-1alpha), Monocyte Chemotactic Protein (MCP-1), platelet-derived growth factor (PDGF), insulin-like growth factors (IGF-1 and IGF-2), megakaryocyte promoting ligand (MPL) and SLK-2. Growth factors are commercially available, for example, from R&D Systems (Minneapolis, Minn.). Particularly preferred are combinations of growth factors, especially the combination of SCF, IL-1 alpha, IL-3 (EP Publ. EP 275,598 and 282,185, incorporated herein by reference) and IL-6. It may also be desirable to selectively remove inhibitors of hematopoiesis using an antibodies, soluble receptors, or the like.

In general, the above-mentioned growth factors are purified or partially purified before they are added to the culture medium. Usually, they will be produced by recombinant DNA methods, but they may also be purified by standard biochemical techniques from conditioned media. Non-naturally-occurring growth factors can also be produced by recombinant DNA methods, for example, PIXY-321 is a fusion protein which has both GM-CSF and IL-3 activity, as described in U.S. Pat. No. 5,108,910, incorporated herein by reference. It will be evident to those skilled in the art that other fusion proteins, combining multiple growth factor activities, can be readily constructed, for example, fusion proteins combining SCF activity with that of other growth factors such as IL-1, IL-3, IL-6, G-CSF, and/or GM-CSF.

The amount of each growth factor to be used is determined empirically and will vary depending on the purity and method of production of the factors. Generally, concentrations between 0.5 and 100 ng/ml are sufficient, more often between 0.5 and 50 ng/ml. Where more than one growth factor is used, the optimum amount of each factor should be determined in combination with the other factors to be used. This is because some growth factors can modulate the activity of other growth factors, necessitating that they be used sequentially rather than simultaneously, while in other instances, growth factors may act synergistically. Still other growth factors may enhance proliferation or differentiation along one pathway, while suppressing another pathway of interest.

Separated precursor cells may be cultured in any vessel which is capable of being sterilized, is adapted or adaptable to gas exchange with the atmosphere, and is constructed of a material which is non-toxic to cells. A variety of vessels suitable for this purpose are well-known in the art, including stirring flasks (Corning, Inc., Corning, N.Y.), stirred tank reactors (Verax, Lebanon, N.H.), airlift reactors, suspension cell retention reactors, cell adsorption reactors, and cell entrapment reactors, petri dishes, multiwell plates, flasks, bags and hollow fiber devices. If agitation is desired, it can be attained by any of a variety of means, including stirring, shaking, airlift, or end-over-end rotation. In addition to maintaining the culture in suspension by agitating the medium (as by stirring or airlift), the culture can also be maintained in suspension by matching the density of the culture medium to the density of the cells or microcarrier beads.

The immortalized human stromal cell lines of the instant invention can be used as feeder layers in ex vivo bone marrow cultures or in colony forming assays, such as the methylcellulose assay for CFU-GM or the cobblestone area forming cell (CAFC) assay. Alternatively, the cell lines of the instant invention may be used to condition medium, which medium may then be used to sustain and/or expand ex vivo cultures of human hematopoietic precursor cells, or to sustain colony forming assays, such as the CFU-GM and CAFC assays. For example, methylcellulose assays are typically performed using conditioned medium from lymphocytes stimulated with the lectin phytohemagglutinin (PHA-LCM). Human stromal cell line conditioned medium (HS-CM) can be substituted for PHA-LCM in methylcellulose assays. Medium conditioned by exposure to the immortalized human stromal cell lines may also be used in vivo to promote hematopoiesis in patients whose bone marrow function is compromised.

Having generally described the invention, the same will be more readily understood by reference to the following examples, which are provided by way of illustration and are not intended as limiting.

EXAMPLE 1

Production of Human Stromal Cell Lines

This Example describes the production and characterization human bone marrow stromal cell lines immortalized from primary donor cells by introduction of the temperature-sensitive A58 SV40 Large-T Antigen. It will be appreciated by those skilled in the art that bone marrow stromal cell lines may also be immortalized by other means, such as, for example, by introduction of the human papilloma virus E6/E7 genes (Rocklein et al., Blood, 85:997–1005 (1995)). In subsequent Examples the stromal cell clones are shown to support the proliferation of hematopoietic progenitors and produce unique profiles of cytokines.

For immortalization of bone marrow cell lines an $\phi_2$ SV40 ecotropic packaging cell line and CR7 amphotropic packaging cell line were used to generate retrovirus producing cells. The SV40 amphotropic retrovirus supernatants were produced according to the following protocol: Viral stocks from supernatants of the $\phi_2$ SV40 ecotropic packaging line were prepared and titered as described below. CR7 amphotropic packaging cells were seeded at $1\times10^6$ cells/per dish into 10-cm dishes one day before infection. On the day of infection, medium was removed and 3 ml supernatant containing $\phi_2$ SV40 ecotropic virus plus protamine sulfate at final concentration 5 µg/ml was added at an MOI of 0.01 cfu/cell (see below). Cells were incubated for 4 hours at 37° C. Next, 10 ml fresh medium was added and cells were incubated for 48 hrs at 37° C. Infected cells were split 1:2 or 1:4 into selective medium containing G418 at 750 µg/ml. Selective medium was changed every 3–4 days, and cells were incubated for a total of 12–14 days after which colonies became obvious. Individual colonies were isolated using cloning cylinders, cells from a single colony were added to 1 well of a 48 well plate. The next day the media in each well was changed and cells were grown to confluence. Clonal cell populations were subsequently split into 1 well of 12 well plate and again grown until confluent. Media was changed again and cells were incubated for 24 hours at 37° C. Supernatants from these cells were used to determine viral titers. Each cell clone was then split to 2 wells of a 6 well plate, grown until 90–95% confluent and frozen until viral titers were determined. The three to four best virus producer clones were then expanded in 6–8 T225 cm² flasks and SV40 amphotropic viral stocks were prepared and titered as described below.

Viral stocks were generated and titered as follows: Virus producing cells were grown to confluence, medium was removed from the cells, discarded, and replaced with a minimum amount of fresh medium. Cells were then cultivated for 24 hours at 37° C. or 48 hours at 33° C. Media supernatant was collected and passed through a 0.45 µm filter. Filtered media was stored at −78° C. or used fresh.

Titer of virus containing supernatants was determined as follows: NIH3T3 target cells ($1\times10^6$ cells/per dish) were seeded into 10-cm dishes one day before infection. On the day of infection, medium was removed from the target cells and 3 ml medium containing virus stock plus polybrene at final concentration of 8 µg/ml was added. From 0.01 microliter to 100 microliter of virus stock ( 3–4 different 10-fold dilutions), depending upon expected titer, was inoculated into the target cell medium and cells were incubated for 4 hours at 37° C. Subsequently, 10 ml fresh medium was added and cells were incubated 48 hours at 37° C. Infected cells were split 1:20 into selective media containing G418 at 750 µg/ml and incubated for 3 days. This medium was replaced with new selective medium and incubated for a total of 10–12 days during which time G418 resistant colonies became obvious. Colonies were counted by staining with Crystal Violet. Titers were determined by counting colonies produced from at least two viral dilutions that differed by 10-fold and produced a countable numbers of colonies. Titers were calculated according to the following formula:

$$G418-R \text{ CFU/ml} = \frac{\text{number of colonies}}{\text{virus volume (ml)} \times \text{replication factor (2)} \times \text{fraction of infected cells plated (1/20)}}$$

For example:

Cells were infected with 50 microliters of virus supernatant, grown 24 hours (replication factor=2 ) and split 1:20 (fraction of infected cells plated ). Number of colonies in first dish was 74 and number in second dish was 68 (average=71). Thus, $\text{titer}_1=1.42\times10^4$ CFU (colony forming units).

2) Cells were infected with 5 microliters of the same virus supernatant, grown 24 hours (replication factor=2 ) and split 1:20 (fraction of infected cells plated). Number of colonies in first dish was 8 and number in second dish was 5 (average=6.5). $\text{Titer}_2=1.3\times10^4$ CFU.

3) TITER=average (Titer$_1$, Titer$_2$)=1.36×10$^4$ CFU.

For infection of cells, the MOI (multiplicity of infection) was determined according to the formula:

$$MOI = \frac{\text{titer of virus (CFU)}}{\text{number of cells}}$$

Fifty milliliters of human unfractionated bone marrow (BM) was obtained from Poietic Technologies, Inc. The bone marrow was treated with ammonium chloride lysis buffer for five minutes at room temperature to remove red cells. The cells were washed twice in phosphate buffered saline then resuspended in Myelocult medium containing hydrocortisone (0.01 µg/ml final concentration) at 2×10$^6$ cells per ml. The cells were seeded into eight 150 mm dishes (approximately 40 ml per dish). The cells were placed in an incubator at 37° C. with 5% CO$_2$ for 3 days. The cells were then transferred to a 32° C. incubator. Half media replacement was performed after the first 10 days of culture and performed every 7 days thereafter. Cells were left in culture until the adherent cell layer became 90% confluent.

Human primary stromal cells were transduced with temperature-sensitive A58 SV40 Large-T Antigen retrovirus as described below: Viral stocks prepared from amphotropic packaging cell clones were inoculated to 0.4×10$^6$ primary stromal cells/10 cm dish incubating at 33° C. (plated the previous day). On the day of infection, media was removed and 3 ml media containing virus stock (MOI=1) plus protamine sulfate at a final concentration of 5 µg/ml was added. Cells were incubated for 4 hours at 37° C., then 10 ml fresh media was added and cells were incubated for 48 hours at 37° C. Media was then changed with fresh media (10 ml) and incubated 48 hours at 37° C. Infected cells were split 1:2 or 1:4 (depending upon properties of the cell's donor and virus stock) into selective media containing G418 at 750 µg/ml and incubated at 33° C. Selective media was changed every 3–4 days, and cells were incubated for a total of 18–21 days at which time colonies became obvious. Clonal populations of cells were then isolated using cloning cylinders and cells from each colony were placed into 1 well of a 48 well plate. The next day the media was changed and cells were subsequently split 1:2 or 1:3 approximately once a week or when necessary. Clonal populations were then expanded and continuously cultured for analysis of their cytokine production and ability to support hematopoiesis. The cell lines HGS2.11, HGS2.52, HGS3.18, HGS3.30, HGS3.65, HGS3.66, HGS3.103, and HGS3.114 were derived using the above procedure.

EXAMPLE 2

Stromal Cell Line Conditioned Media Contain a Unique Profile of Human Cytokines

Immortalized stromal cell lines secrete multiple cytokines (see Table 1 and Detailed Description above). To assess the ability of stromal cells to secrete cytokines, ELISAs (Enzyme Linked-Immuno-Sorbent Assays) were carried out as described below: Tissue culture-treated dishes were precoated with 0.1% gelatin for 1 hour at room temperature. Stromal lines were seeded (1.5×10$^6$ cells/10 cm$^2$ dish or 4×10$^4$ cells/well of 24 well plates) and grown to ~95% confluence at 32° C. in 5% CO$_2$. Cytokine secretion levels were determined using either irradiated or non-irradiated cells grown in modified Whitlock-Witte media (Iscove's Modified Dulbecco's Medium (Life Technologies-Gibco BRL, Gaithersburg, Md., USA) with 10% fetal bovine serum and 5×10$^{-5}$ molar 2-mercaptoethanol) or grown in modified Dexter media (Myelocult media (Stem Cell Technologies, Inc., Vancouver, BC, Canada), MEM alpha base, 12.5% horse serum, 12.5% fetal bovine serum, 0.2 millimolar I-inositol, 20 millimolar folic acid, 1×10$^{-4}$ molar 2-mercaptoethanol, 2 millimolar L-glutamine) with 0.01 micrograms/ml hydrocortisone). To irradiate cells the cell plates were placed in a $^{137}$Cs irradiator (J. L. Shepard & Associates Model Mark 1-68A irradiator) and subjected to a 15 Gray (1500 Rads) dose of radiation. Cell media was immediately removed and replaced with fresh media. After addition of fresh media, the cells were incubated at 37° C. in 5% CO$_2$. Forty-eight hours later the media was removed for ELISA analysis.

ELISA analysis was performed for each cytokine according to the manufacturers directions as indicated below: For detection and quantitation of IL-8, IL-11, FLT3L, SCF, LIF, M-CSF, TGF-beta1, MIP-1alpha, Tpo, MCP-1, and IL-1alpha ELISAs were performed using the corresponding "Quantikine™ Immunoassay" kit according to instructions supplied by the manufacturer (R&D Systems; Minneapolis, Minn.). For detection and quantitation of G-CSF, ELISAs were performed using the "Human G-CSF Quantikine™ HS (High Sensitivity) Immunoassay" according to instructions supplied by the manufacturer (R&D Systems; Minneapolis, Minn.). For detection and quantitation of IL-7, ELISAs were performed using the "Human IL-7 Quantikine™ HS (High Sensitivity) Immunoassay" according to instructions supplied by the manufacturer (R&D Systems; Minneapolis, Minn.). For detection and quantitation of TNF-alpha, ELISAs were performed using the "Human TNF-alpha QuantiGlo™ Immunoassay according to instructions supplied by the manufacturer (R&D Systems; Minneapolis, Minn.). For detection and quantitation of GM-CSF, ELISAs were performed using the Human GM-CSF Cytoscreen™ Immunoassay Kit according to instructions supplied by the manufacturer (BioSource Int.; Cambarillo, Calif.). For detection and quantitation of IL-1beta, ELISAs were performed using the IL-1beta Predicta™ Human Cytokine Assay Kit according to instructions supplied by the manufacturer (Genzyme Diagnostics Corp.; Cambridge, Mass.).

EXAMPLE 3

Immortalized Stromal Lines Support Hematopoiesis

To assess the ability of stromal cells to support hematopoiesis, cobblestone area forming assays were performed as described below: Tissue culture-treated dishes were precoated with 0.1% gelatin for 1 hour at room temperature. Stromal lines were seeded (1.5×10$^6$ cells/10 cm$^2$ dish or 4×10$^4$ cells/well of 24 well plates) and grown to confluence at 32° C. in 5% CO$_2$. Cell plates were then irradiated using a $^{137}$Cesium source (15 Gray) to prevent further mitosis. The media was replaced with fresh media and hematopoietic cells (2×10$^4$ cells/10 cm$^2$ dish or 450–500 cells/well of 24 well plates) were seeded onto the stromal layers and incubated at 37° C. in 5% CO$_2$. The cultures were monitored weekly for the appearance/disappearance of cobblestone areas. Half media replacement was performed weekly. Assays were performed with cells grown in modified Whitlock-Witte media (Iscove's Modified Dulbecco's Medium (Life Technologies-Gibco BRL, Gaithersburg, Md., USA) with 10% fetal bovine serum and 5×10$^{-5}$ molar 2-mercaptoethanol) or grown in modified Dexter media (Myelocult media (Stem Cell Technologies, Inc., Vancouver, BC, Canada); MEM alpha base, 12.5% horse serum, 12.5% fetal bovine serum, 0.2 millimolar I-inositol, 20 millimolar folic acid, $1\times10^{-4}$ molar 2-mercaptoethanol, 2 millimolar L-glutamine) with 0.01 micrograms/ml hydrocortisone). The cell lines HGS2.11, HGS2.52, HGS3.18, HGS3.30, HGS3.65, HGS3.66, HGS3.103, and +HGS3.114 were able to support hematopoiesis, as determined by the above assay, for 3 to 6 weeks in culture (see Table 2).

Microorganism Deposit Information

A deposit of the human stromal cell lines HGS2.11, HGS2.52, HGS3.18, HGS3.30, HGS3.65, HGS3.66, HGS3.103, HGS3.114 were made on Dec. 14, 1999 on behalf of Human Genome Sciences, Inc. (Rockville, Md.) with the American Type Culture Collection, 10801 University Boulevard, Manassas, Va. 20110-2209 under the terms of the Budapest Treaty and designated with the following accession numbers: HGS3.18 was assigned ATCC number PTA-1054, HGS3.66 was assigned ATCC number PTA-1055, HGS2.52 was assigned ATCC number PTA-1056, HGS3.103 was assigned ATCC number PTA-1057, HGS3.114 was assigned ATCC number PTA-1058, HGS2.11 was assigned ATCC number PTA-1059, HGS3.30 was assigned ATCC number PTA-1060, and HGS3.65 was assigned ATCC number PTA-1061.

All publications, patents and foreign patent publications are herein incorporated by reference to the same extent as if each individual publication, patent or patent publication was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A human stromal cell line selected from the group consisting of: HGS2.11 (available from the American Type Culture Collection (ATCC) as Deposit No. PTA-1059), HGS2.52 (available as ATCC Deposit No. PTA-1056), HGS3.18 (available as ATCC Deposit No. PTA-1054), HGS3.30 (available as ATCC Deposit No. PTA-1060), HGS3.65 (available as ATCC Deposit No. PTA-1061), HGS3.66 (available as ATCC Deposit No. PTA-1055), HGS3.103 (available as ATCC Deposit No. PTA-1057), and HGS3.114 (available as ATCC Deposit No. PTA-1058).

2. The human stromal cell line of claim 1, wherein the human stromal cell line is HGS2.11.

3. The human stromal cell line of claim 1, wherein the human stromal cell line is HGS2.52.

4. The human stromal cell line of claim 1, wherein the human stromal cell line is HGS3.18.

5. The human stromal cell line of claim 1, wherein the human stromal cell line is HGS3.30.

6. The human stromal cell line of claim 1, wherein the human stromal cell line is HGS3.65.

7. The human stromal cell line of claim 1, wherein the human stromal cell line is HGS3.66.

8. The human stromal cell line of claim 1, wherein the human stromal cell line is HGS3.103.

9. The human stromal cell line of claim 1, wherein the human stromal cell line is HGS3.114.

* * * * *